United States Patent
Kim et al.

(10) Patent No.: US 10,031,417 B2
(45) Date of Patent: *Jul. 24, 2018

(54) COMPOUND, COLORANT INCLUDING THE SAME, POSITIVE PHOTOSENSITIVE RESIN COMPOSITION INCLUDING THE SAME AND COLOR FILTER

(71) Applicant: SAMSUNG SDI CO., LTD., Yongin-si, Gyeonggi-do (KR)

(72) Inventors: Hyeongmook Kim, Suwon-si (KR); Kyuyoung Kim, Suwon-si (KR); Young Lee, Suwon-si (KR); Myoungyoup Shin, Suwon-si (KR); Seungjib Choi, Suwon-si (KR)

(73) Assignee: Samsung SDI Co., Ltd., Yongin-si, Gyeonggi-do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/372,430

(22) Filed: Dec. 8, 2016

(65) Prior Publication Data

US 2017/0248845 A1    Aug. 31, 2017

(30) Foreign Application Priority Data

Feb. 26, 2016 (KR) .................. 10-2016-0023620

(51) Int. Cl.
| | | |
|---|---|---|
| G02B 5/20 | (2006.01) | |
| G03F 7/004 | (2006.01) | |
| G03F 7/028 | (2006.01) | |
| G02B 5/22 | (2006.01) | |
| C07D 311/82 | (2006.01) | |
| G03F 7/00 | (2006.01) | |
| G03F 7/033 | (2006.01) | |

(52) U.S. Cl.
CPC .......... *G03F 7/0045* (2013.01); *C07D 311/82* (2013.01); *G02B 5/223* (2013.01); *G03F 7/0007* (2013.01); *G03F 7/028* (2013.01); *G03F 7/033* (2013.01)

(58) Field of Classification Search
CPC ..... C07D 311/82; G03F 7/0007; G03F 7/028; G03F 7/033; G02B 5/223; C09B 69/109
USPC .......................................................... 430/7
See application file for complete search history.

(56) References Cited

U.S. PATENT DOCUMENTS

2006/0020141 A1*  1/2006  Banning ............. C07D 311/82
                                                         552/208

FOREIGN PATENT DOCUMENTS

| CN | 103309155 A | | 9/2013 |
|---|---|---|---|
| CN | 104678706 A | * | 6/2015 |
| JP | 4287030 B2 | | 7/2009 |
| JP | 2011-100114 A | | 5/2011 |
| JP | 2011-118368 A | | 6/2011 |
| JP | 2012-032754 A | | 2/2012 |
| JP | 2013-064099 A | | 4/2013 |
| JP | 2013-225132 A | | 10/2013 |
| JP | 2014-012814 A | | 1/2014 |
| JP | 5647279 B2 | | 12/2014 |
| JP | 2015-004968 B1 | | 1/2015 |
| JP | 5772263 B2 | | 9/2015 |
| JP | 2016-065220 A | * | 4/2016 |
| KR | 10-1385175 B1 | | 4/2014 |
| KR | 10-2014-0055575 A | | 5/2014 |
| KR | 10-1402696 B1 | | 6/2014 |
| KR | 10-2015-0061585 | | 6/2015 |
| KR | 10-1523753 B1 | | 6/2015 |
| KR | 10-1523756 B1 | | 6/2015 |
| TW | 201313834 A | | 4/2013 |
| TW | 201502126 A | | 1/2015 |

OTHER PUBLICATIONS

Computer-generated translation of CN 104678706 (Jun. 2015).*
Computer-generated translation of JP 2016-065220 (Apr. 2016).*
Notice of Allowance dated Sep. 25, 2017 of the corresponding Taiwanese Patent Application No. 105142117.
Provisional double patenting rejection over claims of the above-identified application; USPTO Office action dated Dec. 7, 2017, in U.S. Appl. No. 15/404,689.

* cited by examiner

*Primary Examiner* — John A McPherson
(74) *Attorney, Agent, or Firm* — Lee & Morse, P.C.

(57) ABSTRACT

A compound represented by Chemical Formula 1, a colorant including the compound, a photosensitive resin composition including the colorant, and a color filter manufactured using the photosensitive resin composition (in Chemical Formula 1, each substituent is the same as defined in the detailed description),

[Chemical Formula 1]

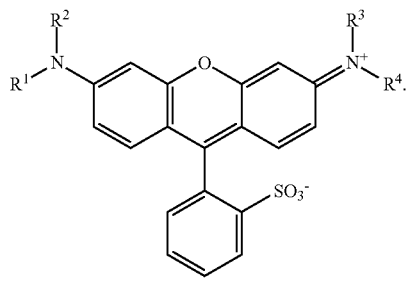

14 Claims, 3 Drawing Sheets

COMPOUND, COLORANT INCLUDING THE SAME, POSITIVE PHOTOSENSITIVE RESIN COMPOSITION INCLUDING THE SAME AND COLOR FILTER

CROSS-REFERENCE TO RELATED APPLICATION

Korean Patent Application No. 10-2016-0023620, filed on Feb. 26, 2016, in the Korean Intellectual Property Office, and entitled: "Novel Compound, Colorant Including the Same, Positive Photosensitive Resin Composition Including the Same and Color Filter," is incorporated by reference herein in its entirety.

BACKGROUND

1. Field

Embodiments relate to a compound, a colorant including the same, a photosensitive resin composition including the same, and a color filter.

2. Description of the Related Art

A liquid crystal display device among many kinds of displays has an advantage of lightness, thinness, low cost, low power consumption for operation, and improved adherence to an integrated circuit and has been more widely used for a mobile phone, a laptop computer, a monitor, and a TV screen.

SUMMARY

Embodiments are directed to a compound represented by Chemical Formula 1.

[Chemical Formula 1]

In Chemical Formula 1,
at least one of $R^1$ to $R^4$ is a group represented by Chemical Formula 2 and the others of $R^1$ to $R^4$ are independently a substituted or unsubstituted C1 to C20 alkyl group or a substituted or unsubstituted C6 to C20 aryl group,

[Chemical Formula 2]

wherein, in Chemical Formula 2,
$R^5$ is a substituted or unsubstituted C1 to C20 alkyl group, a substituted or unsubstituted C3 to C20 cycloalkyl group, a substituted or unsubstituted C6 to C20 aryl group, or a substituted or unsubstituted C2 to C20 heteroaryl group.

$R^1$ to $R^4$ may independently include at least two functional groups represented by Chemical Formula 2.

$R^1$ or $R^2$ may include the functional group represented by Chemical Formula 2.

$R^3$ or $R^4$ may include the functional group represented by Chemical Formula 2.

$R^5$ may be a substituted C1 to C20 alkyl group, a substituted or unsubstituted C3 to C20 cycloalkyl group, or a substituted or unsubstituted C6 to C20 aryl group.

$R^5$ may be represented by Chemical Formula 3 or Chemical Formula 4.

[Chemical Formula 3]

[Chemical Formula 4]

In Chemical Formulae 3 and 4,
$R^6$ to $R^8$ are independently a substituted or unsubstituted C1 to C10 alkyl group, and
A is a substituted or unsubstituted C3 to C10 cycloalkyl group, or a substituted or unsubstituted C6 to C20 aryl group.

The compound represented by Chemical Formula 1 may be represented by one of Chemical Formula 5 to 10.

[Chemical Formula 5]

[Chemical Formula 6]

-continued

[Chemical Formula 7]

[Chemical Formula 8]

[Chemical Formula 9]

[Chemical Formula 10]

The compound represented by Chemical Formula 1 may have maximum absorbance in a wavelength range of 500 nm to 600 nm.

Another embodiment provides a colorant including the compound.

The colorant may be a dye.

The dye may be a red dye, a blue dye, or a violet dye.

Another embodiment provides a photosensitive resin composition including the colorant.

The photosensitive resin composition may further include a binder resin, a photopolymerizable compound, a photopolymerization initiator, and a solvent.

The binder resin may include an acryl-based binder resin, a cardo-based binder resin, or a combination thereof.

Another embodiment provides a color filter manufactured using the photosensitive resin composition.

BRIEF DESCRIPTION OF THE DRAWINGS

Features will become apparent to those of skill in the art by describing in detail example embodiments with reference to the attached drawings in which.

DETAILED DESCRIPTION

Example embodiments will now be described more fully hereinafter with reference to the accompanying drawings;

however, they may be embodied in different forms and should not be construed as limited to the embodiments set forth herein. Rather, these embodiments are provided so that this disclosure will be thorough and complete, and will fully convey example implementations to those skilled in the art. In the drawing figures, the dimensions of layers and regions may be exaggerated for clarity of illustration. Like reference numerals refer to like elements throughout.

As used herein, when specific definition is not otherwise provided, the term "substituted" refers to one substituted with a substituent selected from a halogen (F, Br, Cl, or I), a hydroxy group, a nitro group, a cyano group, an amino group ($NH_2$, $NH(R^{200})$ or $N(R^{201})(R^{202})$, wherein $R^{200}$, $R^{201}$, and $R^{202}$ are the same or different, and are independently a C1 to C10 alkyl group), an amidino group, a hydrazine group, a hydrazone group, a carboxyl group, a substituted or unsubstituted alkyl group, a substituted or unsubstituted alkenyl group, a substituted or unsubstituted alkynyl group, a substituted or unsubstituted alicyclic organic group, a substituted or unsubstituted aryl group, or a substituted or unsubstituted heterocyclic group.

As used herein, when specific definition is not otherwise provided, the term "alkyl group" refers to a C1 to C20 alkyl group, and specifically a C1 to C15 alkyl group, the term "cycloalkyl group" refers to a C3 to C20 cycloalkyl group, and specifically a C3 to C18 cycloalkyl group, the term "alkoxy group" refers to a C1 to C20 alkoxy group, and specifically a C1 to C18 alkoxy group, the term "aryl group" refers to a C6 to C20 aryl group, and specifically a C6 to C18 aryl group, the term "alkenyl group" refers to a C2 to C20 alkenyl group, and specifically a C2 to C18 alkenyl group, the term "alkylene group" refers to a C1 to C20 alkylene group, and specifically C1 to C18 alkylene group, and the term "arylene group" refers to a C6 to C20 arylene group, and specifically a C6 to C16 arylene group.

As used herein, when specific definition is not otherwise provided, "(meth)acrylate" refers to "acrylate" and "methacrylate" and "(meth)acrylic acid" refers to "acrylic acid" and "methacrylic acid."

As used herein, when a definition is not otherwise provided, the term "combination" refers to mixing or copolymerization. In addition, "copolymerization" refers to block copolymerization to random copolymerization, and "copolymer" refers to a block copolymer to a random copolymer.

In the chemical formula of the present specification, unless a specific definition is otherwise provided, hydrogen is bonded at the position when a chemical bond is not drawn where supposed to be given.

In the present specification, a cardo-based resin refers to a resin including at least one functional group selected from Chemical Formula 11-1 to Chemical Formula 11-11 in its backbone.

In the present specification, when specific definition is not otherwise provided, "*" indicates a point where the same or different atom or chemical formula is linked.

An embodiment provides a compound represented by Chemical Formula 1.

[Chemical Formula 1]

In Chemical Formula 1,
at least one of $R^1$ to $R^4$ is a group represented by Chemical Formula 2 and the others of $R^1$ to $R^4$ are independently a substituted or unsubstituted C1 to C20 alkyl group or a substituted or unsubstituted C6 to C20 aryl group,

[Chemical Formula 2]

wherein, in Chemical Formula 2,
$R^5$ is a substituted or unsubstituted C1 to C20 alkyl group, a substituted or unsubstituted C3 to C20 cycloalkyl group, a substituted or unsubstituted C6 to C20 aryl group, or a substituted or unsubstituted C2 to C20 heteroaryl group.

A color filter manufactured by using a pigment-type photosensitive resin composition may have a limit in terms of luminance and a contrast ratio due to a pigment particle size. In addition, a color image sensor device for an image sensor may be improved by using a smaller dispersion particle diameter to form a fine pattern. In order to correspond to such, an attempt to realize a color filter having improved luminance and a contrast ratio has been made by introducing a dye forming no particle instead of the pigment to prepare a photosensitive resin composition appropriate for the dye.

In general, a photosensitive resin composition including a xanthene-based compound in which a charge is separated may have low solubility in an organic solvent such as PGMEA and may show deteriorated heat resistance and chemical resistance. Thus, a xanthene-based compound as a colorant may be limited with respect to use in the photosensitive resin composition.

According to an embodiment, a compound represented by Chemical Formula 1 includes at least one functional group represented by Chemical Formula 2. According to an embodiment, solubility in an organic solvent may be improved and heat resistance may be enhanced, and furthermore a blue-shifted spectrum may be provided and luminance may be improved compared with a general xanthene-based compound.

In an example embodiment, $R^1$ to $R^4$ are independently at least two functional groups represented by Chemical Formula 2. When the compound according to an embodiment includes at least two functional groups represented by Chemical Formula 2, solubility in an organic solvent and luminance of a composition including the compound may be further improved. A compound including one functional group represented by Chemical Formula 2 may be synthesized by adjusting contents of reactants compared with the compound including at least two functional groups represented by Chemical Formula 2 and may be easily synthesized by a person having an ordinary skill in this art by referring to a method of synthesizing the compound including at least two functional groups represented by Chemical Formula 2.

For example, the $R^1$ or $R^2$ may include the functional group represented by Chemical Formula 2.

For example, the $R^1$ or $R^2$ may include the functional group represented by Chemical Formula 2, and simultaneously the $R^3$ or $R^4$ may include the functional group represented by Chemical Formula 2.

$R^5$ may include carbon atoms, and one of the carbon atoms of $R^5$ may be linked to a nitrogen atom of Chemical Formula 2 by a single bond. Herein, the carbon atom linked to a nitrogen atom of Chemical Formula 2 by a single bond i) may not be bonded with a hydrogen atom or ii) may form a cycloalkane ring with other carbon atoms. When the carbon atoms in $R^5$ linked to the nitrogen atom of Chemical Formula 2 by a single bond satisfy the i) or ii) requirement, the compound according to an embodiment has improved heat resistance and improves luminance of a composition including the compound according to the above embodiment.

For example, the $R^5$ may be a substituted C1 to C20 alkyl group or a substituted or unsubstituted cyclic group.

For example, the $R^5$ may be a substituted C1 to C20 alkyl group, a substituted or unsubstituted C3 to C20 cycloalkyl group, or a substituted or unsubstituted C6 to C20 aryl group.

When the $R^5$ is a substituted C1 to C20 alkyl group or a substituted or unsubstituted C6 to C20 aryl group, the carbon atoms in $R^5$ linked to the nitrogen atom of Chemical Formula 2 by a single bond may not bond with a hydrogen atom.

When the $R^5$ is a substituted or unsubstituted C3 to C20 cycloalkyl group, the carbon atoms in $R^5$ linked to the nitrogen atom of Chemical Formula 2 by a single bond may form a cycloalkane ring with other carbon atoms.

For example, the $R^5$ may be represented by Chemical Formula 3 or Chemical Formula 4.

[Chemical Formula 3]

[Chemical Formula 4]

In Chemical Formulae 3 and 4,

$R^6$ to $R^8$ are independently substituted or unsubstituted C1 to C10 alkyl group, A is a substituted or unsubstituted C3 to C10 cycloalkyl group, or a substituted or unsubstituted C6 to C20 aryl group.

For example, Chemical Formula 4 may be represented by Chemical Formula 4-1 or Chemical Formula 4-2.

[Chemical Formula 4-1]

[Chemical Formula 4-2]

In Chemical Formulae 4-1 and 4-2,

$L^1$ is a single bond or a substituted or unsubstituted C1 to C7 alkylene group, and B is a substituted or unsubstituted C6 to C20 aryl group.

The compound represented by Chemical Formula 1 may be represented by one of Chemical Formula 5 to 10, for example.

[Chemical Formula 5]

[Chemical Formula 6]

[Chemical Formula 7]

[Chemical Formula 8]

[Chemical Formula 9]

[Chemical Formula 10]

The compound represented by Chemical Formula 1 may have maximum absorbance in a wavelength range of 500 nm to 600 nm.

Another embodiment provides a polymer formed by a copolymerization reaction of the compound represented by Chemical Formula 1 with a monomer. For example, the monomer may be an ethylenic unsaturated monomer, and in this case, the polymer may be an acrylic polymer.

For example, the ethylenic unsaturated monomer may be an aromatic vinyl compound, a unsaturated carboxylate ester compound, a unsaturated amino alkyl carboxylate ester compound, a vinyl carboxylate ester compound, a unsaturated glycidyl carboxylate ester compound, a vinyl cyanide compound, a unsaturated amide compound, or a combination thereof.

For example, the ethylenic unsaturated monomer may be an aromatic vinyl compound such as styrene, α-methylstyrene, vinyltoluene, vinylbenzylmethylether, and the like; an unsaturated carboxylate ester compound such as methyl (meth)acrylate, ethyl(meth)acrylate, butyl(meth)acrylate, 2-ethylhexyl acrylate, 2-hydroxyethyl(meth)acrylate, 2-hydroxy butyl(meth)acrylate, benzyl(meth)acrylate, cyclohexyl(meth)acrylate, phenyl(meth)acrylate, and the like; an unsaturated amino alkyl carboxylate ester compound such as 2-aminoethyl(meth)acrylate, 2-dimethylaminoethyl(meth) acrylate, and the like; a vinyl carboxylate ester compound such as vinyl acetate, vinyl benzoate and the like; an unsaturated glycidyl carboxylate ester compound such as glycidyl(meth)acrylate, and the like; a vinyl cyanide compound such as (meth)acrylonitrile, and the like; an unsaturated amide compound such as (meth)acrylamide, and the like, or a combination thereof.

An acrylic polymer as a product of a copolymerization of the compound represented by Chemical Formula 1 and the ethylenic unsaturated monomer may provide excellent heat resistance and processibility, and may be useful as a colorant in a photosensitive resin composition for a color filter.

Another embodiment provides a colorant including the compound and/or the acrylic polymer.

The colorant may be a dye, for example a red dye, a blue dye, or a violet dye.

Another embodiment provides a photosensitive resin composition including the colorant.

The photosensitive resin composition may further include a binder resin, a photopolymerizable compound, a photopolymerization initiator, and a solvent.

Hereinafter, each component is specifically described.

Colorant

The colorant may further include an organic solvent-soluble dye in addition to the compound according to an embodiment and/or the compound according to an embodiment and an acrylic polymer.

Examples of the organic solvent-soluble dye may be a triarylmethane-based compound, an anthraquinone-based compound, a benzylidene-based compound, a cyanine-based compound, a phthalocyanine-based compound, an azaporphyrin-based compound, an indigo-based compound, and the like.

The colorant may further include a pigment in addition to the compound and/or the polymer.

The pigment may include a blue pigment, a violet pigment, a red pigment, a green pigment, a yellow pigment, and the like.

Examples of the blue pigment may be C.I. blue pigment 15:6, C.I. blue pigment 15, C.I. blue pigment 15:1, C.I. blue pigment 15:2, C.I. blue pigment 15:3, C.I. blue pigment 15:4, C.I. blue pigment 15:5, C.I. blue pigment 16, C.I. blue pigment 22, C.I. blue pigment 60, C.I. blue pigment 64, C.I. blue pigment 80, or a combination thereof.

Examples of the violet pigment may be C.I. violet pigment 1, C.I. violet pigment 19, C.I. violet pigment 23, C.I. violet pigment 27, C.I. violet pigment 29, C.I. violet pigment 30, C.I. violet pigment 32, C.I. violet pigment 37, C.I. violet pigment 40, C.I. violet pigment 42, C.I. violet pigment 50, or a combination thereof.

Examples of the red pigment may be a perylene-based pigment, an anthraquinone-based pigment, a dianthraquinone-based pigment, an azo-based pigment, a diazo-based pigment, a quinacridone-based pigment, an anthracene-based pigment, and the like. Specific examples of the red pigment may be a perylene pigment, a quinacridone pigment, naphthol AS, a sicomin pigment, an anthraquinone (sudan I, II, III, R), dianthraquinonylate, bis azo, benzopyrane, and the like.

Examples of the green pigment may be a halogenated phthalocyanine-based pigment such as a C.I. pigment green 58.

Examples of the yellow pigment may include a C.I. pigment yellow 139, a C.I. pigment yellow 138, a C.I. pigment yellow 150, and the like, and may be used singularly or as a mixture of two or more.

The pigment may be included in a form of pigment dispersion liquid in the photosensitive resin composition.

The pigment dispersion liquid may include a solid pigment, a solvent, and a dispersing agent in order to disperse the pigment in the solvent uniformly.

The pigment may be included in a solid content of 1 wt % to 20 wt %, for example 8 wt % to 20 wt %, for example 8 wt % to 15 wt %, for example 10 wt % to 20 wt %, for example 10 wt % to 15 wt % based on the total amount of pigment dispersion liquid.

The dispersing agent may be a non-ionic dispersing agent, an anionic dispersing agent, a cationic dispersing agent, and the like. Specific examples of the dispersing agent may be polyalkylene glycol and esters thereof, polyoxyalkylene, polyhydric alcohol ester alkylene oxide addition product, alcoholalkylene oxide addition product, sulfonate ester, sulfonate salt, a carboxylate ester, a carboxylate salt, an alkylamide alkylene oxide addition product, alkyl amine, and the like, and may be used singularly or as a mixture of two or more.

Commercially available examples of the dispersing agent may include DISPERBYK-101, DISPERBYK-130, DISPERBYK-140, DISPERBYK-160, DISPERBYK-161, DISPERBYK-162, DISPERBYK-163, DISPERBYK-164, DISPERBYK-165, DISPERBYK-166, DISPERBYK-170, DISPERBYK-171, DISPERBYK-182, DISPERBYK-2000, DISPERBYK-2001, and the like made by BYK Co., Ltd.; EFKA-47, EFKA-47EA, EFKA-48, EFKA-49, EFKA-100, EFKA-400, EFKA-450, and the like made by EFKA Chemicals Co.; Solsperse 5000, Solsperse 12000, Solsperse 13240, Solsperse 13940, Solsperse 17000, Solsperse 20000, Solsperse 24000GR, Solsperse 27000, Solsperse 28000, and the like made by Zeneka Co.; or PB711, or PB821 made by Ajinomoto Inc.

The dispersing agent may be included in an amount of 1 wt % to 20 wt % based on the total weight of the pigment dispersion liquid. When the dispersing agent is included within the range, dispersion of a photosensitive resin composition is improved due to an appropriate viscosity, and thus optical, physical and chemical quality may be maintained when the photosensitive resin composition is applied to products.

The solvent for forming the pigment dispersion liquid may be ethylene glycol acetate, ethylcellosolve, propylene glycol monomethyl ether acetate, ethyl lactate, polyethylene glycol, cyclohexanone, propylene glycol methylether, and the like.

Binder Resin

The binder resin may be an acryl-based binder resin, a cardo-based binder resin, or a combination thereof. For example, the binder resin may be an acryl-based binder resin.

The acryl-based binder resin may be a copolymer of a first ethylenic unsaturated monomer and a second ethylenic unsaturated monomer that is copolymerizable therewith, and may be a resin including at least one acryl-based repeating unit.

The first ethylenic unsaturated monomer may be an ethylenic unsaturated monomer including at least one carboxyl group. Examples of the monomer include (meth)acrylic acid, maleic acid, itaconic acid, fumaric acid, or a combination thereof.

The first ethylenic unsaturated monomer may be included in an amount of 5 wt % to 50 wt %, for example 10 wt % to 40 wt % based on the total amount of the acryl-based binder resin.

The second ethylenic unsaturated monomer may be an aromatic vinyl compound such as styrene, $\alpha$-methylstyrene, vinyl toluene, vinylbenzylmethylether and the like; an unsaturated carboxylate ester compound such as methyl (meth)acrylate, ethyl(meth)acrylate, butyl(meth)acrylate, 2-hydroxyethyl(meth)acrylate, 2-hydroxy butyl(meth)acrylate, benzyl(meth)acrylate, cyclohexyl(meth)acrylate, phenyl(meth)acrylate, and the like; an unsaturated amino alkyl carboxylate ester compound such as 2-aminoethyl(meth) acrylate, 2-dimethylaminoethyl(meth)acrylate, and the like; a carboxylic acid vinyl ester compound such as vinyl acetate, vinyl benzoate, and the like; an unsaturated glycidyl carboxylate ester compound such as glycidyl(meth)acrylate, and the like; a vinyl cyanide compound such as (meth) acrylonitrile and the like; an unsaturated amide compound such as (meth)acrylamide, and the like; and the like, and may be used singularly or as a mixture of two or more.

Specific examples of the acryl-based binder resin may be a polybenzylmethacrylate copolymer, an acrylic acid/benzylmethacrylate copolymer, a methacrylic acid/benzylmethacrylate copolymer, a methacrylic acid/benzylmethacrylate/styrene copolymer, a methacrylic acid/benzylmethacrylate/2-hydroxyethylmethacrylate copolymer, a methacrylic acid/benzylmethacrylate/styrene/2-hydroxyethylmethacrylate copolymer, and the like, etc. These may be used singularly or as a mixture of two or more.

The acryl-based binder resin may have a weight average molecular weight of 3,000 g/mol to 150,000 g/mol, for example 5,000 g/mol to 50,000 g/mol, for example 20,000 g/mol to 30,000 g/mol. When the acryl-based binder resin has a weight average molecular weight within the range, the photosensitive resin composition may have good physical and chemical properties, appropriate viscosity, and close contacting properties with a substrate during manufacture of a color filter.

The acryl-based binder resin may have an acid value of 15 mgKOH/g to 60 mgKOH/g, for example 20 mgKOH/g to 50 mgKOH/g. When the acryl-based binder resin has an acid value within the range, a pixel pattern may have excellent resolution.

The cardo-based binder resin may include a repeating unit represented by Chemical Formula 11.

[Chemical Formula 11]

In Chemical Formula 11,
$R^{11}$ and $R^{12}$ are independently a hydrogen atom or a substituted or unsubstituted (meth)acryloyloxyalkyl group,
$R^{13}$ and $R^{14}$ are independently a hydrogen atom, a halogen atom or a substituted or unsubstituted C1 to C20 alkyl group, and
$Z^1$ is a single bond, O, CO, $SO_2$, $CR^{15}R^{16}$, $SiR^{17}R^{18}$ (wherein, $R^{15}$ to $R^{18}$ are independently a hydrogen atom or a substituted or unsubstituted C1 to C20 alkyl group) or one of linking groups represented by Chemical Formula 11-1 to Chemical Formula 11-11,

[Chemical Formula 11-1]

[Chemical Formula 11-2]

[Chemical Formula 11-3]

[Chemical Formula 11-4]

[Chemical Formula 11-5]

In Chemical Formula 11-5,
$R^a$ is a hydrogen atom, an ethyl group, $C_2H_4Cl$, $C_2H_4OH$, $CH_2CH=CH_2$, or a phenyl group.

[Chemical Formula 11-6]

-continued

[Chemical Formula 11-7]

[Chemical Formula 11-8]

[Chemical Formula 11-9]

[Chemical Formula 11-10]

[Chemical Formula 11-11]

$Z^2$ is an acid dianhydride residual group, and
m1 and m2 are independently an integer ranging from 0 to 4.

The cardo-based binder resin may include a functional group represented by Chemical Formula 12 at least one terminal end.

[Chemical Formula 12]

In Chemical Formula 12,
$Z^3$ is represented by Chemical Formulae 12-1 to 12-7.

[Chemical Formula 12-1]

In Chemical Formula 12-1, $R^b$ and $R^c$ are independently a hydrogen atom, a substituted or unsubstituted C1 to C20 alkyl group, an ester group, or an ether group.

[Chemical Formula 12-2]

[Chemical Formula 12-3]

[Chemical Formula 12-4]

[Chemical Formula 12-5]

In Chemical Formula 12-5, $R^d$ is O, S, NH, a substituted or unsubstituted C1 to C20 alkylene group, a C1 to C20 alkylamine group, or a C2 to C20 alkenylamine group.

[Chemical Formula 12-6]

[Chemical Formula 12-7]

The cardo-based binder resin may be, for example prepared by mixing at least two of, a fluorene-containing compound such as 9,9-bis(4-oxiranylmethoxyphenyl)fluorene; an anhydride compound such as benzenetetracarboxylic acid dianhydride, naphthalenetetracarboxylic acid dianhydride, biphenyltetracarboxylic acid dianhydride, benzophenonetetracarboxylic acid dianhydride, pyromellitic dianhydride, cyclobutanetetracarboxylic acid dianhydride, perylenetetracarboxylic acid dianhydride, tetrahydrofurantetracarboxylic acid dianhydride, and tetrahydrophthalic anhydride; a glycol compound such as ethylene glycol, propylene glycol, and polyethylene glycol; an alcohol compound such as methanol, ethanol, propanol, n-butanol, cyclohexanol, and benzylalcohol; a solvent-based compound such as propylene glycol methylethylacetate, and N-methylpyrrolidone; a phosphorus compound such as triphenylphosphine; and an amine or ammonium salt compound such as tetramethylammonium chloride, tetraethylammonium bromide, benzyldiethylamine, triethylamine, tributylamine, benzyltriethylammonium chloride.

When the cardo-based binder resin is used with the acryl-based binder resin, a photosensitive resin composition having an excellent close-contacting force, a high resolution, and high luminescence characteristics may be obtained.

The cardo-based binder resin may have a weight average molecular weight of 500 g/mol to 50,000 g/mol, for example 3,000 g/mol to 30,000 g/mol. When the cardo-based binder resin has a weight average molecular weight within the ranges, a satisfactory pattern may be formed without a residue during a manufacture of a color filter and without losing a film thickness during development.

The cardo-based binder resin may have an acid value of 100 mgKOH/g to 140 mgKOH/g.

Photopolymerizable Compound

The photopolymerizable compound may be a mono-functional or multi-functional ester of (meth)acrylic acid including at least one ethylenic unsaturated double bond.

The photopolymerizable compound may enhance polymerization during exposure in a pattern-forming process and form a pattern having excellent heat resistance, light resistance, and chemical resistance due to the ethylenic unsaturated double bond.

Specific examples of the photopolymerizable compound may be ethylene glycol di(meth)acrylate, diethylene glycol di(meth)acrylate, triethylene glycol di(meth)acrylate, propylene glycol di(meth)acrylate, neopentyl glycol di(meth) acrylate, 1,4-butanediol di(meth)acrylate, 1,6-hexanediol di(meth)acrylate, bisphenol A di(meth)acrylate, pentaerythritol di(meth)acrylate, pentaerythritol tri(meth)acrylate, pentaerythritol tetra(meth)acrylate, pentaerythritol hexa(meth) acrylate, dipentaerythritol di(meth)acrylate, dipentaerythritol tri(meth)acrylate, dipentaerythritol penta (meth)acrylate, dipentaerythritol hexa(meth)acrylate, bisphenol A epoxy(meth)acrylate, ethylene glycol monomethylether (meth)acrylate, trimethylol propane tri(meth)acrylate, tris(meth)acryloyloxyethyl phosphate, novolac epoxy (meth)acrylate, and the like.

Commercially available examples of the photopolymerizable compound may be as follows. The mono-functional (meth)acrylic acid ester may include Aronix M-101®, M-111®, M-114® (Toagosei Chemistry Industry Co., Ltd.); KAYARAD TC-110S®, TC-120S® (Nippon Kayaku Co., Ltd.); V-158®, V-2311® (Osaka Organic Chemical Ind., Ltd.), and the like.

Examples of a difunctional (meth)acrylic acid ester may include Aronix M-210®, M-240®, M-6200® (Toagosei Chemistry Industry Co., Ltd.), KAYARAD HDDA®, HX-220®, R-604® (Nippon Kayaku Co., Ltd.), V-260®, V-312®, V-335 HP® (Osaka Organic Chemical Ind., Ltd.), and the like. Examples of a tri-functional (meth)acrylic acid ester may include Aronix M-309®, M-400®, M-405®, M-450®, M-7100®, M-8030®, M-8060® (Toagosei Chemistry Industry Co., Ltd.), KAYARAD TMPTA®, DPCA-20®, DPCA-30®, DPCA-60®, DPCA-120® (Nippon Kayaku Co., Ltd.), V-295®, V-300®, V-360®, V-GPT®, V-3PA®, V-400® (Osaka Yuki Kayaku Kogyo Co. Ltd.), and the like.

These may be used singularly or as a mixture of two or more.

The photopolymerizable compound may be treated with acid anhydride to improve developability.

Photopolymerization Initiator

The photopolymerization initiator may be a generally-used photopolymerization initiator in a photosensitive resin composition, for example an acetophenone-based compound, a benzophenone-based compound, a thioxanthone-based compound, a benzoin-based compound, an oxime-based compound, and the like.

Examples of the acetophenone-based compound may be 2,2'-diethoxy acetophenone, 2,2'-dibutoxy acetophenone, 2-hydroxy-2-methylpropinophenone, p-t-butyltrichloro acetophenone, p-t-butyldichloro acetophenone, 4-chloro acetophenone, 2,2'-dichloro-4-phenoxy acetophenone, 2-methyl-1-(4-(methylthio)phenyl)-2-morpholinopropan-1-one, 2-benzyl-2-dimethylamino-1-(4-morpholinophenyl)-butan-1-one, and the like.

Examples of the benzophenone-based compound may be benzophenone, benzoyl benzoate, methyl benzoyl benzoate, 4-phenyl benzophenone, hydroxy benzophenone, acrylated benzophenone, 4,4'-bis(dimethyl amino)benzophenone, 4,4'-bis(diethylamino)benzophenone, 4,4'-dimethylaminobenzophenone, 4,4'-dichlorobenzophenone, 3,3'-dimethyl-2-methoxybenzophenone, and the like.

Examples of the thioxanthone-based compound may be thioxanthone, 2-methylthioxanthone, isopropyl thioxanthone, 2,4-diethyl thioxanthone, 2,4-diisopropyl thioxanthone, 2-chlorothioxanthone, and the like.

Examples of the benzoin-based compound may be benzoin, benzoin methyl ether, benzoin ethyl ether, benzoin isopropyl ether, benzoin isobutyl ether, benzyldimethylketal, and the like.

Examples of the triazine-based compound may be 2,4,6-trichloro-s-triazine, 2-phenyl 4,6-bis(trichloromethyl)-s-triazine, 2-(3',4'-dimethoxystyryl)-4,6-bis(trichloromethyl)-s-triazine, 2-(4'-methoxynaphthyl)-4,6-bis(trichloromethyl)-s-triazine, 2-(p-methoxyphenyl)-4,6-bis(trichloromethyl)-s-triazine, 2-(p-tolyl)-4,6-bis(trichloro methyl)-s-triazine, 2-biphenyl 4,6-bis(trichloro methyl)-s-triazine, bis(trichloromethyl)-6-styryl-s-triazine, 2-(naphthol-yl)-4,6-bis(trichloromethyl)-s-triazine, 2-(4-methoxynaphthol-yl)-4,6-bis(trichloromethyl)-s-triazine, 2-4-bis(trichloromethyl)-6-piperonyl-s-triazine, 2-4-bis(trichloromethyl)-6-(4-methoxystyryl)-s-triazine, and the like.

Examples of the oxime-based compound may be O-acyloxime-based compound, 2-(O-benzoyloxime)-1-[4-(phenylthio)phenyl]-1,2-octandione, 1-(O-acetyloxime)-1-[9-ethyl-6-(2-methylbenzoyl)-9H-carbazol-3-yl]ethanone, O-ethoxycarbonyl-α-oxyamino-1-phenylpropan-1-one, and the like. Specific examples of the O-acyloxime-based compound may be 1,2-octandione, 2-dimethylamino-2-(4-methylbenzyl)-1-(4-morpholin-4-yl-phenyl)-butan-1-one, 1-(4-phenylsulfanyl phenyl)-butane-1,2-dione 2-oxime-O-benzoate, 1-(4-phenylsulfanyl phenyl)-octane-1,2-dione 2-oxime-O-benzoate, 1-(4-phenylsulfanyl phenyl)-octan-1-one oxime-O-acetate, 1-(4-phenylsulfanyl phenyl)-butan-1-one oxime-O-acetate, and the like.

The photopolymerization initiator may further include a carbazole-based compound, a diketone-based compound, a sulfonium borate-based compound, a diazo-based compound, an imidazole-based compound, a biimidazole-based compound, and the like besides the compound.

The photopolymerization initiator may be used with a photosensitizer capable of causing a chemical reaction by absorbing light and becoming excited and then, transferring its energy.

Examples of the photosensitizer may be tetraethylene glycol bis-3-mercapto propionate, pentaerythritol tetrakis-3-mercapto propionate, dipentaerythritol tetrakis-3-mercapto propionate, and the like.

Solvent

The solvent is a material having compatibility with the compound, the acrylic polymer according to an embodiment, the pigment, the binder resin, the photopolymerizable compound, and the photopolymerization initiator but not reacting therewith.

Examples of the solvent may include alcohols such as methanol, ethanol, and the like; ethers such as dichloroethyl ether, n-butyl ether, diisoamyl ether, methylphenyl ether, tetrahydrofuran, and the like; glycol ethers such as ethylene glycol monomethylether, ethylene glycol monoethylether, and the like; cellosolve acetates such as methyl cellosolve acetate, ethyl cellosolve acetate, diethyl cellosolve acetate, and the like; carbitols such as methylethyl carbitol, diethyl carbitol, diethylene glycol monomethylether, diethylene glycol monoethylether, diethylene glycol dimethylether, diethylene glycol methylethylether, diethylene glycol diethylether, and the like; propylene glycol alkylether acetates such as propylene glycol methylether acetate, propylene glycol propylether acetate, and the like; aromatic hydrocarbons such as toluene, xylene and the like; ketones such as methylethylketone, cyclohexanone, 4-hydroxy-4-methyl-2-pentanone, methyl-n-propylketone, methyl-n-butylketone, methyl-n-amylketone, 2-heptanone, and the like; saturated aliphatic monocarboxylic acid alkyl esters such as ethyl acetate, n-butyl acetate, isobutyl acetate, and the like; lactate esters such as methyl lactate, ethyl lactate, and the like; oxy acetic acid alkyl esters such as oxy methyl acetate, oxy ethyl acetate, butyl oxyacetate, and the like; alkoxy acetic acid alkyl esters such as methoxy methyl acetate, methoxy ethyl acetate, methoxy butyl acetate, ethoxy methyl acetate, ethoxy ethyl acetate, and the like; 3-oxy propionic acid alkyl esters such as 3-oxy methyl propionate, 3-oxy ethyl propionate, and the like; 3-alkoxy propionic acid alkyl esters such as 3-methoxy methyl propionate, 3-methoxy ethyl propionate, 3-ethoxy ethyl propionate, 3-ethoxy methyl propionate, and the like; 2-oxy propionic acid alkyl esters such as 2-oxy methyl propionate, 2-oxy ethyl propionate, 2-oxy propyl propionate, and the like; 2-alkoxy propionic acid alkyl esters such as 2-methoxy methyl propionate, 2-methoxy ethyl propionate, 2-ethoxy ethyl propionate, 2-ethoxy methyl propionate, and the like; 2-oxy-2-methyl propionic acid esters such 2-oxy-2-methyl methyl propionate, 2-oxy-2-methyl ethyl propionate, and the like, monooxy monocarboxylic acid alkyl esters of 2-alkoxy-2-methyl alkyl propionates such as 2-methoxy-2-methyl methyl propionate, 2-ethoxy-2-methyl ethyl propionate, and the like; esters such as 2-hydroxy ethyl propionate, 2-hydroxy-2-methyl ethyl propionate, hydroxy ethyl acetate, 2-hydroxy-3-methyl methyl butanoate, and the like; ketonate esters such as ethyl pyruvate, and the like. Additionally, high boiling point solvent such as N-methylformamide, N,N-dimethylformamide, N-methylformanilide, N-methylacetamide, N,N-dimethylacetamide, N-methylpyrrolidone, dimethylsulfoxide, benzylethylether, dihexylether, acetylacetone, isophorone, caproic acid, caprylic acid, 1-octanol, 1-nonanol, benzylalcohol, benzyl acetate, ethyl benzoate, diethyl oxalate, diethyl maleate, γ-butyrolactone, ethylene carbonate, propylene carbonate, phenyl cellosolve acetate, and the like may be also used.

Considering miscibility and reactivity, glycol ethers such as ethylene glycol monoethylether, and the like; ethylene glycol alkylether acetates such as ethyl cellosolve acetate, and the like; esters such as 2-hydroxy ethyl propionate, and the like; carbitols such as diethylene glycol monomethylether, and the like; propylene glycol alkylether acetates such as propylene glycol methylether acetate, propylene glycol propylether acetate and the like may be preferably used.

The photosensitive resin composition may further include an epoxy compound in order to improve close-contacting properties with a substrate.

Examples of the epoxy compound may include a phenol novolac epoxy compound, a tetramethyl biphenyl epoxy compound, a bisphenol A epoxy compound, an alicyclic epoxy compound, or a combination thereof.

The epoxy compound may be included in an amount of 0.01 parts by weight to 20 parts by weight and for example, 0.1 parts by weight to 10 parts by weight based on 100 parts by weight of the photosensitive resin composition. When the epoxy compound is included within the ranges, close-contacting properties, storage properties, and the like may be improved.

In addition, the photosensitive resin composition may further include a silane coupling agent having a reactive substituent such as a carboxyl group, a methacryloyl group, an isocyanate group, an epoxy group, and the like to improve its adherence to a substrate.

Examples of the silane-based coupling agent may include trimethoxysilyl benzoic acid, γ-methacryl oxypropyl trimethoxysilane, vinyl triacetoxysilane, vinyl trimethoxysilane, γ-iso cyanate propyl triethoxysilane, γ-glycidoxy propyl trimethoxysilane, β-(3,4-epoxycyclohexyl)ethyltrimethoxysilane, and the like. These may be used singularly or in a mixture of two or more.

The silane-coupling agent may be included in an amount of 0.01 parts by weight to 10 parts by weight based on 100 parts by weight of the photosensitive resin composition. When the silane-coupling agent is included within the range, close-contacting properties, storing properties, and the like may be excellent.

In addition, the photosensitive resin composition may further include a surfactant in order to improve coating properties and prevent a defect if necessary.

The surfactant may be a fluorine-based surfactant, and examples of the fluorine-based surfactant may be F-482, F-484, F-478, F-554, and the like of DIC Co., Ltd., but are not limited thereto.

The surfactant may be used in an amount of 0.001 parts by weight to 5 parts by weight based on 100 parts by weight of the photosensitive resin composition. When the surfactant is included within the ranges, excellent wetting on a glass substrate as well as coating uniformity may be secured, but a stain may not be produced.

Furthermore, the photosensitive resin composition may include other additives such as an antioxidant, a stabilizer, and the like in a predetermined amount unless they deteriorate properties of the photosensitive resin composition.

According to an embodiment, a color filter manufactured using the photosensitive resin composition is provided.

A pattern-forming process in the color filter may be as follows.

An example process includes coating the positive photosensitive resin composition on a support substrate in a method of spin coating, slit coating, inkjet printing, and the like; drying the coated positive photosensitive resin composition to form a photosensitive resin composition film; exposing the positive photosensitive resin composition film to light; developing the exposed positive photosensitive resin composition film in an alkali aqueous solution to obtain a photosensitive resin film; and heat-treating the photosensitive resin film.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Synthesis of Compound

Synthesis Example 1: Synthesis of Compound Represented by Chemical Formula 8 compound A                    compound B

-continued compound B chemical formula 8

32 g of a compound A (CAS No. 77545-45-0) was put in a reactor and dissolved in 300 g of 2-propanol. Subsequently, 28.2 g of 2-ethylamino ethanol was added thereto, and the mixture was stirred at 80° C. for 8 hours. The reactant was cooled down, and 2 L of water was added thereto to produce a precipitate. The obtained precipitate was vacuum-filtered and additionally washed with water. The filtered product was dried to obtain 32 g of a compound B (80% of a yield).

10 g of the compound B was put in a reactor, 30 g of dimethyl formamide and 4.5 g of butylisocyanate were added thereto, and the mixture was stirred for 8 hours.

Synthesis Example 2: Synthesis of Compound Represented by Chemical Formula 9

10 g of the compound B was put in a reactor, 30 g of dimethyl formamide and 5.6 g of cyclohexylisocyanate were added thereto, and the mixture was stirred for 8 hours. 100 g of dichloromethane was added to the reactant, and the resultant was washed. The obtained organic layer was silica-filtered and distilled under a reduced pressure. The distilled mixture was dissolved in 10 g of dichloromethane, and the solution was added to 100 g of normal hexane in a dropwise fashion for a precipitation. The obtained precipitate was vacuum-filtered and additionally washed. The filtered product was dried to obtain 11.3 g of a compound represented by Chemical Formula 9 (73% of a yield).

[Chemical Formula 9]

Subsequently, 100 g of dichloromethane was added to the reactant, and the resultant was washed. Then, an organic layer therefrom was silica-filtered and distilled under a reduced pressure. The distilled mixture was dissolved in 10 g of dichloromethane, and the solution was added to 100 g of normal hexane in a dropwise fashion for a precipitation. The obtained precipitate was vacuum-filtered and additionally washed. The filtered product was dried to obtain 11.2 g of a compound represented by Chemical Formula 8 (81% of a yield).

Maldi-TOF MS: 708.3 m/z

Maldi-TOF MS: 760.4 m/z

Synthesis Example 3: Synthesis of Compound Represented by Chemical Formula 10

10 g of the compound B was put in a reactor, 30 g of dimethyl formamide and 5.3 g of phenylisocyanate were added thereto, and the mixture was stirred for 8 hours. 100 g of dichloromethane was added to the reactant, and the resultant was washed. The obtained organic layer was silica-filtered and distilled under a reduced pressure. The distilled mixture was dissolved in 10 g of dichloromethane, and the solution was added to 100 g of normal hexane in a dropwise fashion for precipitation. The obtained precipitate was vacuum-filtered and additionally washed. The filtered product was dried to obtain 4.8 g of a compound represented by Chemical Formula 10 (33% of a yield).

[Chemical Formula 10]

Maldi-TOF MS: 748.3 m/z

Evaluation 1: Solubility Measurement 0.5 g of each compound according to Synthesis Examples 1 to 3 was respectively added to diluting solvents (MeOH, $CH_2Cl_2$, cyclohexanone), each solution was stirred with a rotary mixer (Mixrotar VMR-5, Iuchi Seieido Co., Ltd.) at 25° C. and 100 rpm for 1 hour, and then, the dissolution state of each compound (the amount of the compound dissolved in the solvents) was examined, and the results are provided in Table 1.

TABLE 1

| | Amount of dissolved compound (wt %) | | |
|---|---|---|---|
| | MeOH | $CH_2Cl_2$ | Cyclohexanone |
| Chemical Formula 5 | >7% | >7% | 3% |
| Chemical Formula 6 | >7% | >7% | 3% |
| Chemical Formula 7 | >7% | >7% | 2% |
| Chemical Formula 8 | >10% | >10% | 5% |
| Chemical Formula 9 | >10% | >10% | 5% |
| Chemical Formula 10 | >10% | >10% | 3% |

Referring to Table 1, the compounds represented by Chemical Formulae 5 to 10 according to an embodiment exhibited excellent solubility in an organic solvent.

Synthesis of Photosensitive Resin Composition

Example 1

The photosensitive resin composition of Example 1 was prepared by mixing the following components to have a composition shown in Table 2.

Specifically, a photopolymerization initiator was dissolved in a solvent, the solution was stirred at room temperature for 2 hours, an acryl-based binder resin and a photopolymerizable compound were added thereto, and the mixture was stirred at room temperature for 2 hours. Subsequently, the compound represented by Chemical Formula 5 and a pigment (a pigment dispersion liquid) as a colorant were added to the reactant, and the mixture was stirred at room temperature for one hour. Then, a product therefrom was three times filtered to remove impurities to prepare a photosensitive resin composition.

TABLE 2

| | | | (unit: wt %) |
|---|---|---|---|
| | | Materials | Amount |
| Colorant | Dye | Compound represented by Chemical Formula 5 | 5.0 |
| | Pigment dispersion liquid | Pigment Y138 pigment dispersion liquid | 15.0 |
| Alkali soluble resin | | A/B = 15/85 (w/w), molecular weight (Mw) = 22,000 g/mol A: methacrylic acid B: benzylmethacrylate | 3.5 |
| Photopolymerizable compound | | Dipentaerythritolhexaacrylate (DPHA) | 8.0 |
| Photopolymerization initiator | | 1,2-octandione | 1.0 |
| | | 2-dimethylamino-2-(4-methyl-benzyl)-1-(4-morpholin-4-yl-phenyl)-butan-1-one | 0.5 |
| Solvent | | cyclohexanone | 37.0 |
| | | PGMEA (Propylene Glycol Monomethyl Ether Acetate) | 30.0 |
| Total | | | 100.00 |

Example 2

A photosensitive resin composition was prepared according to the same method as Example 1 except for using the compound represented by Chemical Formula 6 instead of the compound represented by Chemical Formula 5.

Example 3

A photosensitive resin composition was prepared according to the same method as Example 1 except for using the compound represented by Chemical Formula 7 instead of the compound represented by Chemical Formula 5.

Example 4

A photosensitive resin composition was prepared according to the same method as Example 1 except for using the compound represented by Chemical Formula 8 according to Synthesis Example 1 instead of the compound represented by Chemical Formula 5.

Example 5

A photosensitive resin composition was prepared according to the same method as Example 1 except for using the compound represented by Chemical Formula 9 according to Synthesis Example 2 instead of the compound represented by Chemical Formula 5.

Example 6

A photosensitive resin composition was prepared according to the same method as Example 1 except for using the compound represented by Chemical Formula 10 according to Synthesis Example 3 instead of the compound represented by Chemical Formula 5.

Comparative Example 1

A photosensitive resin composition was prepared according to the same method as Example 1 except for using a red pigment (SC-P541-4214, Toyo Ink LLC.) instead of the compound represented by Chemical Formula 5.

Evaluation 2: Measurement of Heat Resistance

Figure 1:
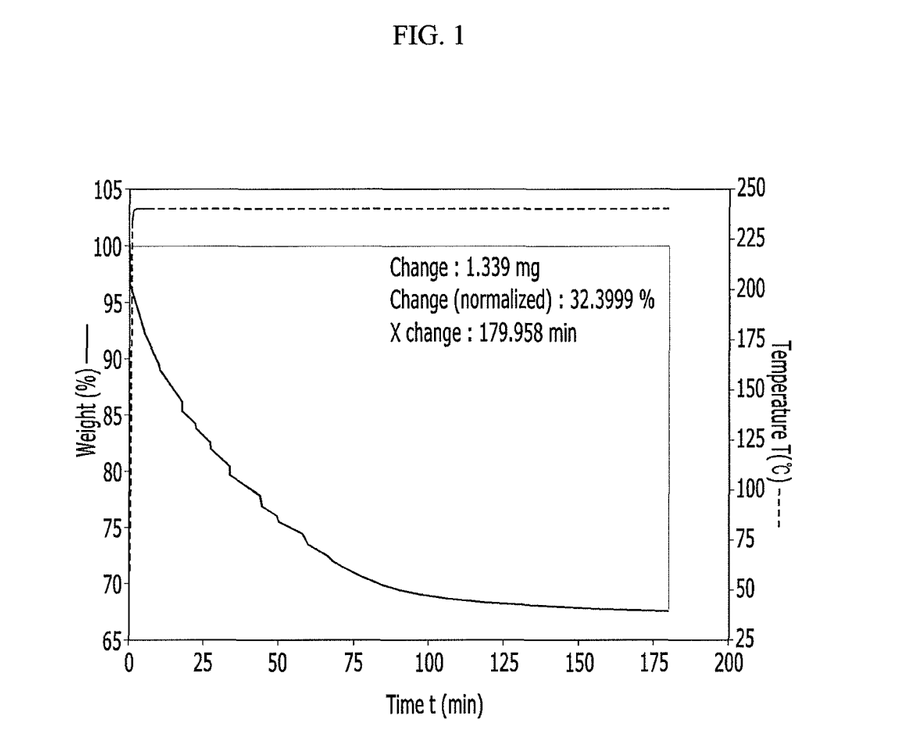
FIG. 1 illustrates a TGA graph of the compound of Chemical Formula 8 according to Synthesis Example 1.
Figure 2:
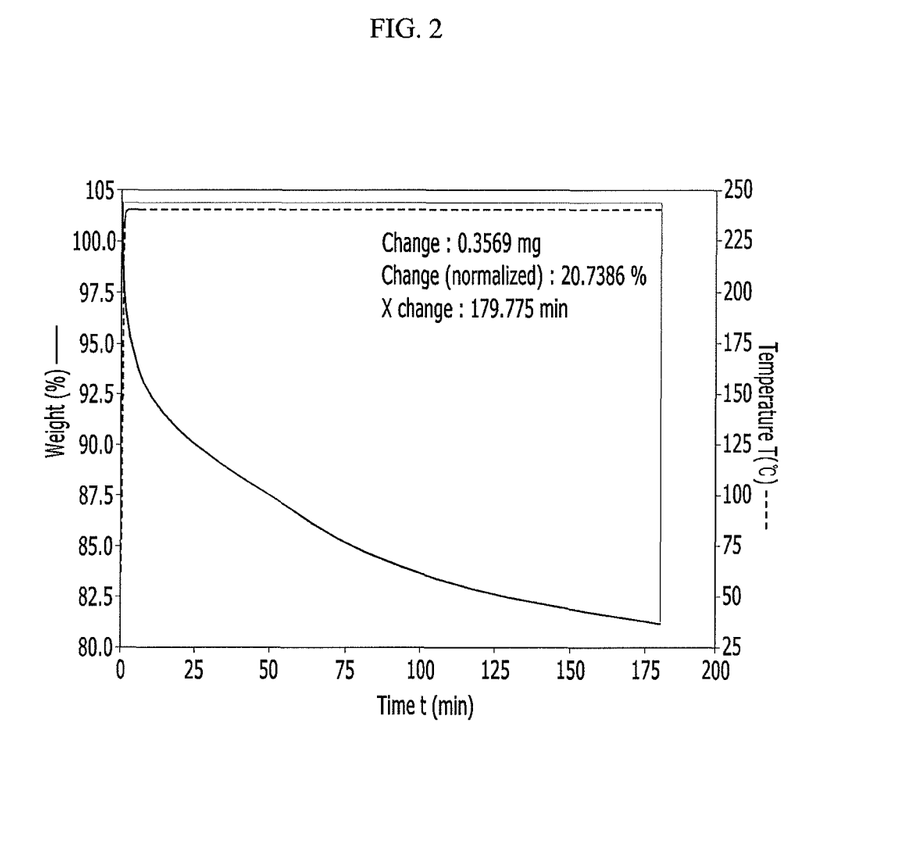
FIG. 2 illustrates a TGA graph of the compound of Chemical Formula 9 according to Synthesis Example 2.
Figure 3:
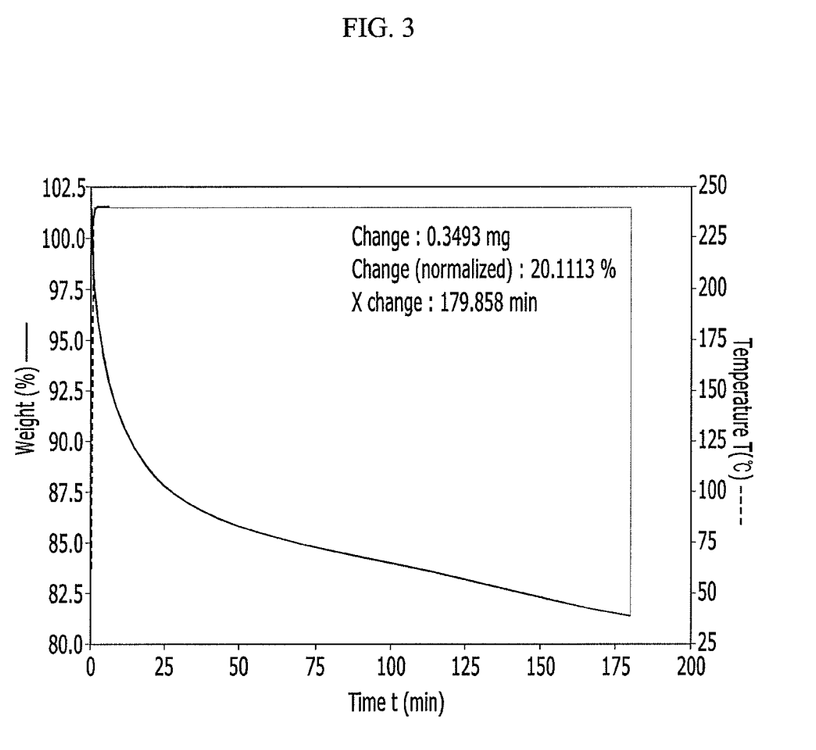
FIG. 3 illustrates a TGA graph of the compound of Chemical Formula 10 according to Synthesis Example 3.

TGA graphs of the compounds represented by Chemical Formulae 8 to 10 according to Synthesis Examples 1 to 3 were shown in FIGS. 1 to 3. Referring to FIGS. 1 to 3, the compounds represented by Chemical Formulas 8 to 10 exhibited excellent heat resistance.

Evaluation 3: Measurement of Luminance

The photosensitive resin compositions according to Examples 1 to 6 and Comparative Example 1 were respectively coated to be 1 μm to 3 μm thick on a 1 mm-thick degreased glass substrate and dried on a 90° C. hot plate for 2 minutes to obtain films. The films were exposed by using a high pressure mercury lamp having a main wavelength of 365 nm. Subsequently, the films were dried in a 200° C. forced convection drying furnace for 5 minutes to obtain samples. A color coordinate and luminance (Y) of pixel layers of the samples were measured by using a spectrophotometer (MCPD3000, Otsuka Electronics Co., Ltd.), and the results are provided in Table 3. A color coordinate (Gx) and the luminance (Y) were calculated with a reference to a color coordinate (Gy).

TABLE 3

|  | Luminance (Y) |
|---|---|
| Example 1 | 14.21 |
| Example 2 | 14.18 |
| Example 3 | 14.20 |
| Example 4 | 14.59 |
| Example 5 | 14.55 |
| Example 6 | 14.57 |
| Comparative Example 1 | 13.90 |

Referring to Table 3 and FIGS. 1 to 3, the photosensitive resin compositions of Examples 1 to 6 including a compound according to an embodiment as a colorant exhibited excellent luminance and heat resistance compared with the photosensitive resin composition of Comparative Example 1 including no compound according to an embodiment.

By way of summation and review, a liquid crystal display device includes a lower substrate on which a black matrix, a color filter, and an ITO pixel electrode are formed, and an upper substrate on which an active circuit portion including a liquid crystal layer, a thin film transistor, and a capacitor layer and an ITO pixel electrode are formed. Color filters are formed in a pixel region by sequentially stacking a plurality of color filters (in general, formed of three primary colors such as red (R), green (G), and blue (B)) in a predetermined order to form each pixel, and a black matrix layer is disposed in a predetermined pattern on a transparent substrate to form a boundary between the pixels. The pigment dispersion method that is one of methods of forming a color filter provides a colored thin film by repeating a series of processes such as coating a photopolymerizable composition including a colorant on a transparent substrate including a black matrix, exposing a formed pattern to light, removing a non-exposed part with a solvent, and thermally curing the same. A coloring photosensitive resin composition used for manufacturing a color filter according to the pigment dispersion method generally includes an alkali soluble resin, a photopolymerization monomer, a photopolymerization initiator, a solvent, other additives, and the like and additionally, an epoxy resin and the like. The pigment dispersion method is actively applied to manufacture an LCD such as a mobile phone, a laptop, a monitor, and TV. However, the photosensitive resin composition for a color filter using the pigment dispersion method having many merits has some drawbacks, since there are difficulties in minutely pulverizing of a powder, requiring various additives for stabilizing a dispersion liquid even if dispersed and complex processes, and further maintaining optimal quality of a pigment dispersion liquid under complicated storage and transportation conditions. In addition, a color filter manufactured by using a pigment-type photosensitive resin composition has a limit in luminance and a contrast ratio due to a pigment particle size. Accordingly, development of a dye having similar heat resistance and chemical resistance to those of a pigment is desired.

As described above, a compound according to an embodiment may exhibit excellent heat resistance, and thus a photosensitive resin composition including a colorant including the compound as a constituent element may be used to manufacture a color filter having excellent luminance, and the like.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A compound represented by Chemical Formula 1:

[Chemical Formula 1]

wherein, in Chemical Formula 1,
at least one of $R^1$ to $R^4$ is a group represented by Chemical Formula 2 and the others of $R^1$ to $R^4$ are independently a substituted or unsubstituted C1 to C20 alkyl group or a substituted or unsubstituted C6 to C20 aryl group,

[Chemical Formula 2]

wherein, in Chemical Formula 2,
$R^5$ is an alkyl-substituted C1 to C20 alkyl group, a substituted or unsubstituted C3 to C20 cycloalkyl group, or a substituted or unsubstituted C6 to C20 aryl group.

2. The compound as claimed in claim 1, wherein the $R^1$ to $R^4$ independently include at least two functional groups represented by Chemical Formula 2.

3. The compound as claimed in claim 1, wherein the $R^1$ or $R^2$ includes the functional group represented by Chemical Formula 2.

4. The compound as claimed in claim 3, wherein the $R^3$ or $R^4$ includes the functional group represented by Chemical Formula 2.

5. The compound as claimed in claim 1, wherein the $R^5$ is represented by Chemical Formula 3 or Chemical Formula 4:

[Chemical Formula 3]

[Chemical Formula 4]

wherein, in Chemical Formulae 3 and 4,
$R^6$ to $R^8$ are independently a substituted or unsubstituted C1 to C10 alkyl group, and
A is a substituted or unsubstituted C3 to C10 cycloalkyl group, or a substituted or unsubstituted C6 to C20 aryl group.

6. The compound as claimed in claim 1, wherein the compound represented by Chemical Formula 1 is represented by one of Chemical Formula 5 to 10:

[Chemical Formula 5]

[Chemical Formula 6]

[Chemical Formula 7]

[Chemical Formula 8]

-continued

[Chemical Formula 9]

[Chemical Formula 10]

7. The compound as claimed in claim 1, wherein compound represented by Chemical Formula 1 has maximum absorbance in a wavelength range of 500 nm to 600 nm.

8. A colorant comprising the compound as claimed in claim 1.

9. The colorant as claimed in claim 8, wherein the colorant is a dye.

10. The colorant as claimed in claim 9, wherein the dye is a red dye, a blue dye, or a violet dye.

11. A photosensitive resin composition comprising the colorant as claimed in claim 10.

12. The photosensitive resin composition as claimed in claim 11, wherein the photosensitive resin composition further includes a binder resin, a photopolymerizable compound, a photopolymerization initiator, and a solvent.

13. The photosensitive resin composition as claimed in claim 12, wherein the binder resin includes an acryl-based binder resin, a cardo-based binder resin, or a combination thereof.

14. A color filter manufactured using the photosensitive resin composition as claimed in claim 11.

* * * * *